United States Patent
List et al.

(10) Patent No.: US 11,071,819 B2
(45) Date of Patent: Jul. 27, 2021

(54) VALVE DRIVE UNIT WITH SHAPE MEMORY ALLOY ACTUATOR

(71) Applicant: Roche Diabetes Care, Inc., Indianapolis, IN (US)

(72) Inventors: Hans List, Oberzent (DE); Stefan Pfalz, Weinheim-Lützelsachsen (DE); Niklaus Schneeberger, Köniz (CH); Pierre Jaquier, Billens (CH); Peter Siegrist, Jegenstorf (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 179 days.

(21) Appl. No.: 16/196,435

(22) Filed: Nov. 20, 2018

(65) Prior Publication Data
US 2019/0083706 A1    Mar. 21, 2019

Related U.S. Application Data

(63) Continuation of application No. PCT/EP2017/063440, filed on Jun. 2, 2017.

(30) Foreign Application Priority Data

Jun. 7, 2016    (EP) ..................... 16173361

(51) Int. Cl.
*A61M 5/168*    (2006.01)
*A61M 5/145*    (2006.01)
(Continued)

(52) U.S. Cl.
CPC ...... *A61M 5/16813* (2013.01); *A61M 5/1452* (2013.01); *A61M 5/14248* (2013.01);
(Continued)

(58) Field of Classification Search
CPC .............. F16K 1/221; F16K 31/025; A61M 2205/0266; A61M 2205/3327; A61M 2005/14268
See application file for complete search history.

(56) References Cited

U.S. PATENT DOCUMENTS 6,656,158 B2    12/2003  Mahoney et al.
7,226,278 B2    6/2007   Nason et al.
(Continued)

FOREIGN PATENT DOCUMENTS

EP    1970677 A1    9/2008
EP    2163273 A1    3/2010
(Continued)

OTHER PUBLICATIONS

International Search Report and Written Opinion of the International Searching Authority, PCT/EP2017/063440, dated Nov. 8, 2017, 13 pages.
(Continued)

*Primary Examiner* — Bhisma Mehta
*Assistant Examiner* — James D Ponton
(74) *Attorney, Agent, or Firm* — Bose McKinney & Evans LLP (57) ABSTRACT

Disclosed is a valve drive unit that has first and second SMA wires that can be alternatively activated. The valve drive unit further includes a pivoting member pivotably arranged around a pivoting member axis, the pivoting member including a valve driver arranged at a distance from the pivoting member axis. The first and second SMA wires are coupled to the pivoting member such that an activation of the first SMA wire causes the pivoting member to pivot into a first direction and an activation of the second SMA wire causes the pivoting member to pivot into a second direction, the second direction being opposite to the first direction. The
(Continued)

valve driver is configured to releasably engage a valve driver coupler of a valve unit, such that, in the engaged state, a pivoting of the pivoting member is transmitted to the valve driver coupler via the valve driver.

15 Claims, 5 Drawing Sheets

(51) Int. Cl.
*F16K 1/22* (2006.01)
*A61M 5/142* (2006.01)
*F16K 31/02* (2006.01)

(52) U.S. Cl.
CPC ............ *F16K 1/221* (2013.01); *F16K 31/025* (2013.01); *A61M 2205/0266* (2013.01); *A61M 2205/3327* (2013.01)

(56) References Cited

U.S. PATENT DOCUMENTS

| | | | |
|---|---|---|---|
| 2004/0068985 A1* | 4/2004 | Mernoe | A61M 5/142 60/527 |
| 2008/0077081 A1* | 3/2008 | Mounce | A61M 5/1413 604/67 |
| 2008/0254340 A1 | 10/2008 | Blakey et al. | |
| 2010/0021311 A1 | 1/2010 | McNally et al. | |
| 2010/0242303 A1* | 9/2010 | Callahan | F16K 15/20 36/28 |
| 2011/0009814 A1 | 1/2011 | Tsoukalis | |
| 2011/0224644 A1 | 9/2011 | Haueter et al. | |
| 2011/0319862 A1 | 12/2011 | Friedman et al. | |
| 2012/0184195 A1 | 7/2012 | Browne et al. | |
| 2013/0197438 A1 | 8/2013 | Yang et al. | |
| 2015/0300519 A1* | 10/2015 | Da Pont | F16K 31/56 251/11 |

FOREIGN PATENT DOCUMENTS

| | | |
|---|---|---|
| EP | 2 239 486 A1 | 10/2010 |
| EP | 2 332 599 A2 | 6/2011 |
| EP | 2881128 A1 | 6/2015 |
| JP | 2010-501283 A | 1/2010 |
| JP | 2010-524190 A | 7/2010 |
| RU | 2447905 C2 | 4/2012 |
| WO | WO 99/38551 | 8/1999 |
| WO | WO 2007/095093 A2 | 8/2007 |
| WO | WO 2008/024814 A2 | 2/2008 |
| WO | WO 2011/101641 A2 | 8/2011 |

OTHER PUBLICATIONS

International Preliminary Report on Patentabilty, PCT/EP2017/063440, dated Dec. 11, 2018, 9 pages.

* cited by examiner

VALVE DRIVE UNIT WITH SHAPE MEMORY ALLOY ACTUATOR

RELATED APPLICATIONS

This application is a continuation of PCT/EP2017/063440, filed Jun. 2, 2017, which claims priority to EP 16 173 361.3, filed Jun. 7, 2016, both of which are hereby incorporated herein by reference in their entirety.

BACKGROUND

The present disclosure is related to the field of ambulatory infusion pumps. It is particularly related to drive units for such devices, as well as to dosing units. Ambulatory infusion pumps for infusing a liquid drug into a patient's body over an extended time period are carried by a patient substantially continuously.

Ambulatory infusion pumps are well known in the art for example in the therapy of Diabetes Mellitus by Continuous Subcutaneous Insulin Infusion (CSII) as well as in pain therapy or cancer therapy and are available from a number of suppliers.

According to a classic and well-established design, those ambulatory infusion pumps or systems are typically of the syringe-driver type. A number of drawbacks of such devices are known in the art. In particular, they have a limited precision because they involve delivering very small drug amounts, typically in the nanoliter range, directly out of a drug cartridge as primary drug reservoir, having an overall drug volume in the milliliter range. Therefore, additional concepts and architectures have been proposed which use a dedicated dosing unit downstream from the primary drug reservoir, comprising, e.g., a micro membrane pump or a micro piston. Those dosing units are designed for precise metering of small volumes. While several designs for such dosing units are known in the art, they are rather complex. Most of them are expensive and/or critical with respect to large scale manufacture.

EP1970677A1 discloses a system with a miniaturized metering piston pump with a dosing cylinder that is repeatedly coupled to and filled from a larger primary drug reservoir, followed by coupling the dosing cylinder to an infusion site and infusing the liquid drug out of the dosing cylinder in incremental steps, typically in the nanoliter or microliter range, and over an extended time period of, e.g., a number of hours up to more than a day, in dependence of the patient's specific therapeutic needs. When the dosing cylinder is emptied, it is filled again from the primary drug reservoir. After emptying the primary drug reservoir, both the metering pump and the primary drug reservoir may be discarded and replaced. For alternatively coupling the dosing cylinder to the reservoir and the infusion site, a valve system is proposed. The present document is based on a design of an infusion pump device in accordance with EP1970677A1.

EP2163273A1 discloses a dosing unit according to the principles established by EP1970677A1. According to the EP2163273A1, the dosing unit is—typically releasably—coupled to a single drive unit which is used for both piston movement and valve switching in dependence of the piston position. Valve switching is achieved by moving, e.g., rotating, the dosing cylinder of the dosing unit relative to a stationary valve member, thus establishing alternative fluid communication of the dosing cylinder with either an inlet or an outlet. The valve switching does in particular not involve a liquid administration towards the patient, which is achieved via piston displacement.

EP2881128A1 discloses, in accordance with EP1970677A1, a design where the valve switching and the piston movement are carried out via separate drives with separate dedicated actuators, rather than a common actuator. While requiring some additional hardware effort, critical design issues are avoided and the overall control structure is simplified.

Since the dosing unit is generally a disposable of considerably shorter lifetime as compared to the drive arrangements and further functional units, such as user interface and control circuitry, a modular design is required for cost reasons, where the dosing unit can be separately replaced. For such a modular design that is also assumed in the context of the present disclosure, simple and fault-tolerant coupling and decoupling by a largely untrained and potentially visually and/or motor impaired user is required.

It is desirable to allow safe and defined coupling of the valve and the piston with the associated valve drive unit and pump drive unit, respectively, without requiring the involved interface structures to be in a specific and well-defined reference state. In this context, the EP2881128A1 discloses a design where the valve and the valve drive unit couple via a step switching mechanism.

SUMMARY

As noted above, it is desirable to improve the state of the art regarding drive units and in particular valve drive units for a dosing unit. This disclosure teaches a valve drive unit (also referred to herein as "valve drive") that is compact and of robust design and can favorably be manufactured in a cost-efficient way.

The advantageous valve drive of this disclosure is in particular achieved using a valve drive with SMA (Shape Memory Alloy) wires as actuators. The SMA wires act on a pivoting member that transforms a length variation (contracting and lengthening of the SMA wires) into a rotational movement that is transferred, via an interface structure, to the valve unit of the dosing unit.

The use of SMA actuators in the context of ambulatory infusion pumps, for example insulin pumps, is generally known, for example, from US20130197438A1, U.S. Pat. Nos. 7,226,278B2, 6,656,158B2, US20110319862A1, US20110009814A1, and WO9938551A1. According to these documents, an SMA actuator is used directly for the drug dosing. In some cases, a dosing valve is opened and closed via an SMA actuator, wherein drug is administered as long as the valve is opened.

According to this disclosure, in contrast, an SMA actuator is used for controlling the switching of a control valve that couples the dosing cylinder of the dosing unit alternatively with the patient, e.g., via an infusion line, or with a drug cartridge or generally a primary drug reservoir. The valve switching and accordingly actuation of the SMA actuator, however, does itself not result in any drug administration. Instead, drug administration is controlled by the separate pump drive unit, with the dosing cylinder and the piston forming a positive displacement metering pump as established and proven design.

In an aspect, the valve drive unit may especially be designed for use as part of a drive unit (also referred to as "drive assembly") and in combination with a dosing unit as explained further below. The valve drive unit includes a first SMA wire and a second SMA wire, wherein the first and second SMA wires can be alternatively activated.

The valve drive unit further includes a pivoting member. The pivoting member is pivotably arranged around a pivoting member axis. The pivoting member includes a valve driver. The valve driver is arranged at a distance from the pivoting member axis.

The first and second SMA wires are coupled to the pivoting member such that an activation of the first SMA wire causes the pivoting member to pivot in a first direction and an activation of the second SMA wire causes the pivoting member to pivot in a second direction, the second direction being opposite to the first direction. For coupling of the first and second SMA wires, the pivoting member includes first and second SMA coupling structures.

The valve driver is designed to releasably engage a valve driver coupler of a valve unit, such that, in the engaged state, a pivoting of the pivoting member is transmitted to the valve driver coupler via the valve driver. As explained further below in more detail, the releasable engagement may especially be a releasable meshing engagement. The coupling between valve driver and the valve driver coupler is such that the transfer function between the valve driver and the valve driver coupler is continuous, i.e., a continuous (pivoting) movement of the valve driver results in a corresponding continuous movement of the valve driver coupler, in contrast to a step switching mechanism with a discontinuous transfer function.

As will be explained in more detail further below, the pivoting member transforms a linear movement, in particular a contraction or extension of the SMA wires into a corresponding pivoting of the pivoting member. The pivoting member accordingly serves as transforming member. Because the valve driver is an integral part of the pivoting member, a pivoting of the pivoting member also results in a pivoting of the valve driver around the pivoting member axis on a (circular) path that is determined by the distance between the pivoting member axis and the valve driver.

SMA wires allow the generation of a large (pulling) force when they contract upon being heated (typically via their electric resistance when a driving current flows through the wire), but can be passively strained or lengthened with little force below the activation temperature. In many applications, it is a disadvantage of SMA actuators that the usable stroke length upon contraction is small and in a range of a few percent of the wire length at the most. For this reason, the use of SMA actuators is impossible in many applications, or complex mechanical kinematics are required in order to amplify the stroke length. A valve drive unit in accordance with the present disclosure, in contrast, can be realized in a compact way and with a low number of components.

Each of the first and second SMA wires contracts, after having previously been passively expanded, upon being activated by means of heating the SMA wire with an electric current, striving to return to its memorized shape and length. In operation, the current is provided to the first and second SMA wires such that, at any point in time, only the first SMA wire, only the second SMA wire, or none of the first and second SMA wire is activated, but not both of them at the same time. For this purpose, the valve drive may include corresponding valve drive control circuitry. In this document, the expressions "memorized shape" and "memorized length" refer to the design-given shape and length to which the SMA wires strive to return upon being heated to the activation temperature. While not being essential, the memorized shape of the SMA wires is typically straight or close to straight.

In addition to the pivoting member, the first and second SMA wires are each coupled to a fixed support structure and accordingly act between the pivoting member and the support structure.

In the context of operating a valve unit of a dosing unit as discussed further below in more detail, a pivoting of the pivoting member and the valve driver into the first direction results in a shutoff body of the valve unit moving into a filling position. Similarly, a pivoting of the pivoting member and the valve driver into the second direction results in the shutoff body moving into a draining position. Switching between the filling position and the draining position is accordingly achieved by selectively activating the first and the second SMA wires. In an embodiment, the valve driver is a meshing pin.

The first and second SMA wires may be made from any suited SMA material as known in the art, in particular copper-aluminium-nickel or nickel-titanium, but may also be made by alloying other materials such as zinc, copper, gold and iron. Typically, the first and second SMA wires are of identical design and dimensioning, resulting in a symmetric setup.

In an embodiment, the valve drive does, as such, not include blocks that would limit the pivoting of the pivoting member in an end position. Instead, pivoting of the pivoting member is, in operation, limited by valve blocks of the valve unit. Similarly, in typical embodiments no catches, latches or the like are required for maintaining the pivoting member in a pre-determined position.

In an embodiment, the arrangement of the first and second SMA wires is such that an activation of the first SMA wire lengthens the second SMA wire and an activation of the second SMA wire lengthens the first SMA wire. In such embodiment, one of the first and second SMA wire is, in a stationary situation where none of the SMA wires is activated, in a contracted state (with a minimum length) while the other of the first and second SMA wire is in a lengthened or strained state (with a maximum length). In operation, the state of the first and second SMA wires is reversed with each valve switching between the inlet position and the draining position of the shutoff body. This arrangement is advantageous in so far as no further counter-force elements, such as springs, are required for expanding the SMA wires.

In an embodiment, the pivoting member includes a first SMA coupling structure and a second SMA coupling structure. The first SMA coupling structure couples to the first SMA wire and the second SMA coupling structure couples to the second SMA wire. The first and second SMA coupling structures are further arranged on opposite sides of the pivoting member axis.

In an embodiment, the first and second SMA wires each are U-shaped. In such embodiment, the base of the U-shaped SMA wires (the area where both legs of the "U" meet) is coupled to the pivoting member, while the free ends of both legs are coupled to the support structure. Via the first and second SMA coupling structure, the first and second SMA wire are accordingly deflected or folded back by e.g., 180°. Typically, both legs are parallel for each of the first and second SMA wire. Further typically, the legs of both U-shaped SMA wires are parallel. Further typically, the U-shape is symmetric, with both legs having the same length.

The U-shaped form of this type of embodiment results in a "folding" of the first and second SMA wire in halves. In this way, the total forces that are exerted by the legs sum up and the total pulling force is accordingly doubled for a U-shaped arrangement as compared to an SMA wire having the length of a single leg. For a given required total force, thinner SMA wires may accordingly be used, with the electric resistance increasing with decreasing diameter. Further, since the electric resistance depends on the total length of the SMA-wires, the electric resistances of a U-shaped arrangement is accordingly double the electric resistance of a single leg of identical diameter. The folded design accordingly results in a comparatively high electric resistance, which is favorable in order to limit the required current for heating. In principle, also another folding, e.g., a threefold folding (resulting in an "N-shape") or a fourfold folding (resulting in an "M-shape") would be possible. Such arrangements, however, are typically less favorable in view of the required overall installation space and general design constraints.

In all of these arrangements where the first and second SMA wires are deflected or folded back by the pivoting member, the pivoting member is, fully or in an area of coupling with the SMA wires, favorably made from metal, metal coated or generally conductive. This has the favorable effect that the considerably deformed part of the SMA wires where they are deflected and folded back is electrically shortcut by the pivoting member. Consequently, at least most of the heating current does not flow through this part of the SMA wires, but through the pivoting member. For a U-shaped design of the SMA wires the major current flow is accordingly from one of the legs via the pivoting member to the other leg and not via the base of the U. The deformed base is accordingly, in contrast to the legs not heated to the activation temperature. Thereby, the mechanical load of the SMA wires is significantly reduced.

In a variant, the two legs of a U-shaped SMA wire may be replaced by two separate pieces of SMA wire. Similarly, an N-shape or M-shape arrangement may be replaced by three or four separate pieces of SMA wire, respectively.

In an embodiment, the first SMA wire is coupled to a support structure (also referred to herein as "support") via a first spring structure and the second SMA wire is coupled to the support structure via a second spring structure. As will be explained in more detail in the following, coupling via a spring structure is favorable to prevent an overload and accordingly a damage of the valve actuator that may otherwise occur under adverse circumstances.

In an embodiment where the first and second SMA wires are U-shaped as explained before, the first and second spring structure may each comprise two separate spring elements (also referred to herein as "springs"), with each spring element individually coupling one leg of an SMA wire to the support structure. In an example, the spring elements are leaf springs that are at an end firmly coupled to the support structure, e.g., by screwing or riveting.

Typically, the first and second spring structure, and in an embodiment with four spring elements as explained before, all four spring elements are of identical design and dimensioning, resulting in a symmetric setup.

In an embodiment, the first spring structure is arranged to maintain a coupling between the first SMA wire and the first spring structure in a constant position for a force that is exerted by the first SMA wire below a first threshold force. Likewise, the second spring structure is arranged to maintain a coupling between the second SMA wire and the second spring structure in a constant position for a force that is exerted by the second SMA wire below a second threshold force. Beyond the pulling force that is exerted by the first and second SMA exceeding the first and second threshold forces, respectively, the first and second spring elements are deflected. In a typical embodiment, the first and second threshold forces are chosen to be identical.

In an embodiment, the first spring structure limits a force that may be exerted by the first SMA wire and the second spring structure limits a force that may be exerted by the second SMA wire.

It is to be understood that the memorized length of the SMA wire that corresponds to the memorized shape is subject to manufacturing tolerances. Also, the required contraction of the first and second SMA wire is determined by a number of dimensions that are subject to tolerances. To address this situation, the memorized length of the SMA wires must be selected such that it is shorter than the minimum length that can be practically assumed in operation. In an operational state, further movement of the pivoting member is blocked upon the shutoff-body of the valve unit assuming either of its end positions, i.e., the filling position or the draining position. Since the SMA wires further strive at above their activation temperatures to assume their memorized length, a rigid coupling of the SMA wires to the support structure results in a steep force increase, potentially even damaging the SMA wire and the valve drive unit as a whole. Such overload situation is prevented by the coupling via spring structures in that the coupling between the SMA wires and the spring structures is allowed to move if the force exceeds the threshold force.

An overload situation in which the force needs to be limited may, in addition to the before-discussed situation where further movement is blocked, especially occur under adverse environmental conditions, in particular at high temperatures, e.g., storing temperatures that may be above an activation temperature of the SMA wires, resulting in a contraction of both the first and second SMA wire. The resulting overload may damage the whole valve driver, and cause, e.g., the SMA wires to rip. In such situation, the elastic coupling via the spring structure favorably limits the force.

Favorably, a fixed support member is provided for each of the spring elements and the spring elements are arranged to rest on the fixed support and to be lifted off from the support member upon being deflected. The support members may be part of or rigidly attached to the support structure. In the neutral state, each of the spring elements rests on its support member with a pre-set nominal contact force that corresponds to the threshold force as mentioned before. Upon one of the first and second SMA wires being activated and therefore contracting, the contact force of the corresponding spring elements is reduced by the pulling force that is exerted by the activated SMA wires, with the spring elements still resting on their support members without being deflected. Only upon the contact force becoming zero, the corresponding spring elements are lifted off and are accordingly deflected. The deflection is towards the pivoting member, thereby reducing the distance between the coupling and the pivoting member. In operation, this situation occurs with respect to either of the first and second SMA wire upon the shutoff-body of the valve unit assuming either of its end positions and further movement of the pivoting member being accordingly blocked. It further occurs with respect to both the first and second SMA wires if the environmental temperature exceeds the activation temperature of the SMA wires.

In an embodiment, the first spring structure serves as switch element to interrupt a current supply of the first SMA wire upon a force that is exerted by the first SMA wire on the support structure exceeding a first switching force. Similarly, the second spring structure serves as switch element to interrupt a current supply of the second SMA wire upon a force that is exerted by the second SMA wire on the support structure exceeding a second switching force. In an embodiment, the first and second switching force correspond to the first and second threshold force as explained before.

The first and second switching force are design-given and typically identical. The first and second switching forces are selected somewhat larger as compared to the force that needs to be exerted by an SMA wire for valve actuation, but smaller than the maximum pulling force that may be exerted by the SMA wires without damage. As discussed above and further below in more detail, valve blocks are typically provided that limit the movement of the shutoff body to a range between the filling position and the draining position, respectively, as end positions. As explained before, the contact force becomes zero if either of the end positions is reached, with further contracting of the activated SMA wire resulting in the associated spring elements being lifted off and losing contact with their support member(s). For the here-discussed type of embodiment, the current is provided to the first and second SMA wires by the first and second spring structures, respectively, the spring elements, and the associated supports. A spring element losing contact with its associated support accordingly results in the current supply to the SMA wire being interrupted. Interruption of the current supply is favorably subsequently detected by the valve drive control circuitry which, in turn, switches off and disables the current and power supply of the SMA wire. The first and second switching force for this type of embodiment are given by the nominal contact forces between spring elements and support members as explained before.

Since SMA-based actuators are activated by heating of SMA elements, in the present context SMA wires, energy efficiency is a general topic of concern and in particular in the context of battery-powered applications, like ambulatory infusion pumps. For an acceptable degree of efficiency, fast heating of the SMA wires to or beyond the activation temperature is generally desirable in order to limit thermal losses. Fast heating calls for a large current. Upon further movement being blocked and further contraction of an SMA wire to the memorized length being prevented, the electric energy that is provided to the SMA wires is fully converted into thermal loss energy. The before-mentioned type of embodiment with the spring structure serving as switch ensures a quick interruption of the power supply in the end positions. Therefore, a favorably large current can be used without causing excessive losses. Furthermore, automatic switching off prevents the SMA wires from being damaged by heating beyond a temperature limit where it loses its favorable material properties.

In a further aspect, the drive unit is used in combination with a dosing unit that includes a metering pump unit and a valve unit. The drive unit includes a pump drive unit (also referred to herein as "pump drive"). The pump drive unit includes a pump actuator and a pump driver that is coupled to the pump actuator. The pump driver is designed to releasably engage a piston of the metering pump unit for transmitting a pump driving force and/or pump driving torque from the pump actuator to the piston, thus displacing the piston in a dosing cylinder of the metering pump unit. The drive unit further includes a valve drive unit as discussed above and further below. The phrase "metering pump unit" (also referred to herein as "metering pump") indicates that the unit is suited and designed for administering well-defined volumes in a controlled way. In a typical design that is assumed in the following, the pump unit is a positive displacement pump of the syringe-type where the administered volume is given as the product of the (controllable and/or measurable) piston displacement and the cross-sectional area of the piston.

The coupling of the pump driver and the piston is such that the piston is, in dependence of the pump driving force and/or pump driving torque, displaced in a proximal or an opposite distal direction.

Releasable coupling of the dosing unit and the drive unit allows the design of a modular ambulatory infusion pump with a durable unit that includes the drive unit and may include a user interface, control circuitry, and the like, and a separate disposable unit that is designed for a single application of, e.g., a number of days only and may include the dosing unit and a liquid drug reservoir. Such embodiment is assumed here and in the following. In contrast to the disposable unit, the durable unit—also referred to as pump device further below—is typically designed for an extended lifetime of typically several months or even years.

The phrase "releasable coupling" accordingly refers to a design that allows mechanical coupling and decoupling of the dosing unit and the drive unit (also referred to as "drive assembly"), with the decoupling not causing damage to at least the drive unit. For this purpose, corresponding mechanical mounting structures may be provided at both the dosing unit and the drive unit as will be described further below.

The pump drive and the valve drive are functionally separate in that an activation of the pump drive unit does not affect the valve drive unit and vice versa. The pump actuator only moves the pump driver and the first and second SMA wires as valve actuator only move the pivoting member and the valve driver. In other words, the drive unit is designed to separately control the valve unit and the metering pump unit of the dosing unit.

The drive unit may further include circuitry for controlling the valve drive and the pump drive. While not being essential, the pump actuator is typically a rotatory actuator, such as a standard DC motor, a stepper motor or a brushless DC motor. The control circuitry may be designed to control the pump drive unit and the valve drive unit to control the repeated execution of:

a) Controlling the valve drive unit to move the shutoff body of a valve unit of the dosing unit into a filling position;
b) Controlling, with the shutoff body being in the filling position, the pump drive unit to move the piston inside the dosing cylinder of the metering pump unit into a distal direction, thus increasing a filling volume of the dosing cylinder and filling the dosing cylinder with liquid drug;
c) Controlling the valve drive unit to move the shutoff body from the filling position into a draining position;
d) Controlling, with the shutoff body being in the draining position, the pump drive unit to move the piston inside the dosing cylinder of the metering pump unit in a number of discrete or incremental dosing steps into a proximal direction, thus decreasing the filling volume of the dosing cylinder and dosing liquid drug out of the dosing cylinder.

In such a sequence, the dosing steps are carried out in accordance with therapeutic dosing requirements and may include the dosing of a drug amount on demand in a short time period and/or the dosing of drug increments over an extended time period according to an e.g., pre-programmed or continuously modified dosing schedule. The control logic is further such that piston movements (activation of the pump actuator) and shutoff body movements (activation of either of the first or second SMA wires) do not occur in parallel, but only sequentially.

In an embodiment, the method includes, in a step (b1) that is executed between steps (b) and (c), controlling, with the shutoff body being in the filling position, the pump drive unit to move the piston inside the dosing cylinder of the metering pump unit into the proximal direction, thus pre-tensioning the valve drive system. By this step, the considerable slack that may be present in the system is compensated for.

In an embodiment, the design of the drive unit is such that the pump driver engages the piston and the valve driver engages the valve driver coupler via a common relative engagement movement between the drive unit and the dosing unit. The engagement movement may especially be a linear relative movement between the drive unit and the dosing unit.

Decoupling of the drive unit and the dosing unit is favorably carried out by a linear relative displacement movement in the opposite direction. Such decoupling movement favorably disengages the pump driver and the piston, as well as the valve driver and the valve driver coupler.

The drive unit may further include and/or be operatively coupled to other components that are typically present in an ambulatory infusion pump, such as general control circuitry and a power supply. The drive unit may in particular include and/or be operatively coupled to monitoring circuitry and/or one or monitoring sensors for monitoring the state of the pump drive unit and/or the valve drive unit, such as a valve state. The drive unit may further include and/or be operatively coupled to monitoring circuitry and/or one or more monitoring sensors for monitoring the state of the piston and or the valve state of the dosing unit during operation. The control circuitry is typically based on one or more microcontroller(s) and or microcomputer(s) with corresponding firmware and/or software code. The control circuitry may also include an e.g., wireless communication interface, a display, an acoustic and/or tactile alarm device, and one or more input elements, such as push buttons. The control circuitry may especially be designed to control the repeated execution of a sequence as explained before.

According to a further aspect, a dosing unit is designed to releasably couple to a drive unit as explained above and further below. The dosing unit includes a metering pump unit. The metering pump unit includes a dosing cylinder and a piston. The piston is arranged in sealing sliding engagement inside the dosing cylinder. The piston is further designed to engage, in the coupled state, with the pump driver of the drive unit. For this purpose, the piston may especially include a pump driver coupler.

The dosing unit further includes a valve unit, the valve unit having a filling port, the filling port being designed for fluid coupling with a liquid drug reservoir, a draining port, the draining port being designed for fluid coupling with an infusion site interface, and a shutoff body, the shutoff body being pivotable between a filling position where it fluidly couples the filling port with the dosing cylinder and an alternative draining position where it fluidly couples the dosing cylinder with the draining port.

The dosing unit further includes a valve driver coupler. The valve driver coupler is coupled to or integral with the shutoff body and is designed to engage, in the coupled state, with the valve driver of the drive unit such that a pivoting of the pivoting member is transmitted to the valve driver coupler via the valve driver.

The coupling between valve driver and the valve driver coupler is such that the transfer function between the valve driver and the valve driver coupler is continuous, i.e., a continuous (pivoting) movement of the valve driver results in a corresponding continuous movement of the valve driver coupler and accordingly a continuous movement of the shutoff body.

Further aspects of the dosing unit are discussed above and/or further below in the context of exemplary embodiments. It is important that the pump driver coupler and the valve driver coupler as interface structure to the pump drive unit and the valve drive unit are structurally and functionally distinct and a movement of the piston does not cause a movement of the shutoff body, and vice versa. The valve unit is further designed such that movement between the filling position and the draining position does not involve the movement or displacement of liquid. Valve switching is accordingly displacement free.

In an embodiment, the valve driver coupler includes a funnel-shaped engagement structure. The engagement structure aligns the valve driver coupler and the valve driver with respect to each other during a relative engagement movement between the drive unit and the dosing unit.

During the engagement movement between drive unit and dosing unit, the valve driver of the valve drive unit, for example a meshing pin as explained before, first enters the funnel-shaped engagement structure in its widest section. Upon the engagement movement advancing, the meshing pin moves to a narrower and narrower section of the engagement structure, and the clearance between the meshing pin and the walls of the engagement structure is narrowed. If required by the relative positions of the meshing pin and the engagement structure, the meshing pin is automatically positioned and aligned by the engagement structure. In an end section, the funnel-shaped engagement structure may have parallel walls at a distance to each other such that the meshing pin is, at the end of the engagement movement, situated between the sidewalls of the engagement structure with little slackness or play. The engagement movement accordingly simultaneously serves as alignment movement that aligns the valve driver and the valve driver coupler with respect to each other. During subsequent operation, the valve driver coupler follows the movement of the valve driver.

Any movement of the meshing pin during the engagement movement is associated with a corresponding change in the length of the first and second SMA wire. At this point, it is favorable that an activated (heated) SMA wire may exert a large pulling force, while a non-activated SMA wire may be passively deformed and in particular lengthened (stretched) with little force.

In an embodiment, the valve unit includes valve blocks, the valve blocks blocking a further pivoting of the shutoff body upon assuming the filling position and the draining position.

Alternatively or additionally, valve driver blocks may be provided as part of the valve drive unit and limit the movement of the valve driver, in particular in case it is not coupled to a dosing unit.

In a further aspect, an ambulatory infusion pump includes a drive unit and a dosing unit as discussed above and further below. In a typical embodiment of an insulin pump, the ambulatory infusion pump further includes a drug reservoir with a filling volume of, e.g., 1.5 ml to 3 ml of liquid insulin formulation. In an example of an insulin pump, the dosing unit has a typical filling volume (maximum filling volume of the dosing cylinder) in a range of 0.05 ml to 0.2 ml, for example 0.075 ml in a specific example.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

It is to be noted that in the following description, terms indicating a direction, position, or orientation, such as "left," "right," "upper, lower," "top," "bottom," "proximal," "distal" are merely intended to improve the reader's understanding and exclusively refer to the figures. They do not imply any particular directions or orientations for the application.

Figure 1A:
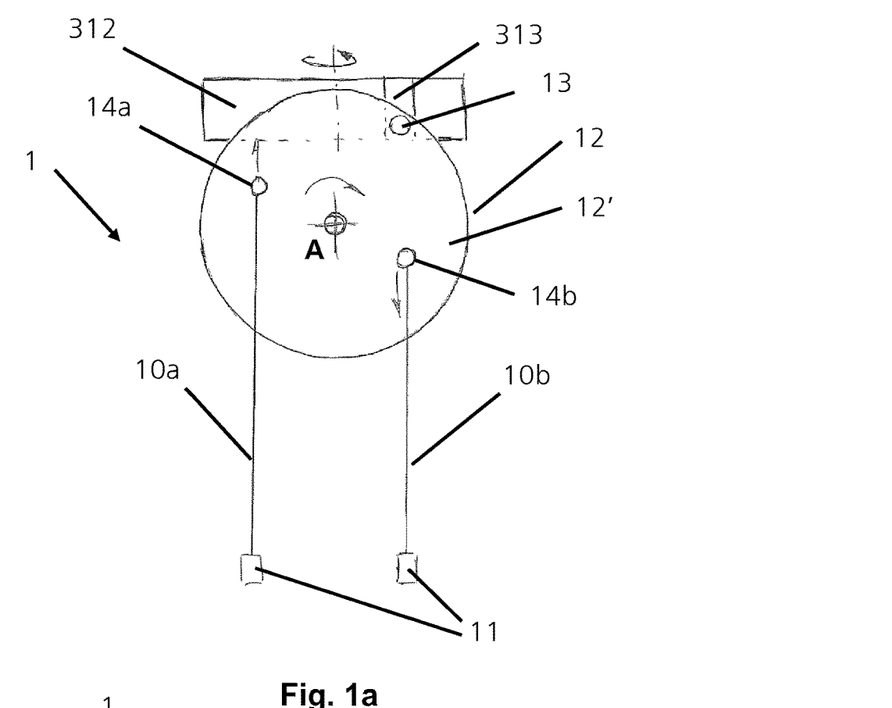
FIGS. 1a, 1b show an exemplary embodiment of a valve drive.
Figure 1B:
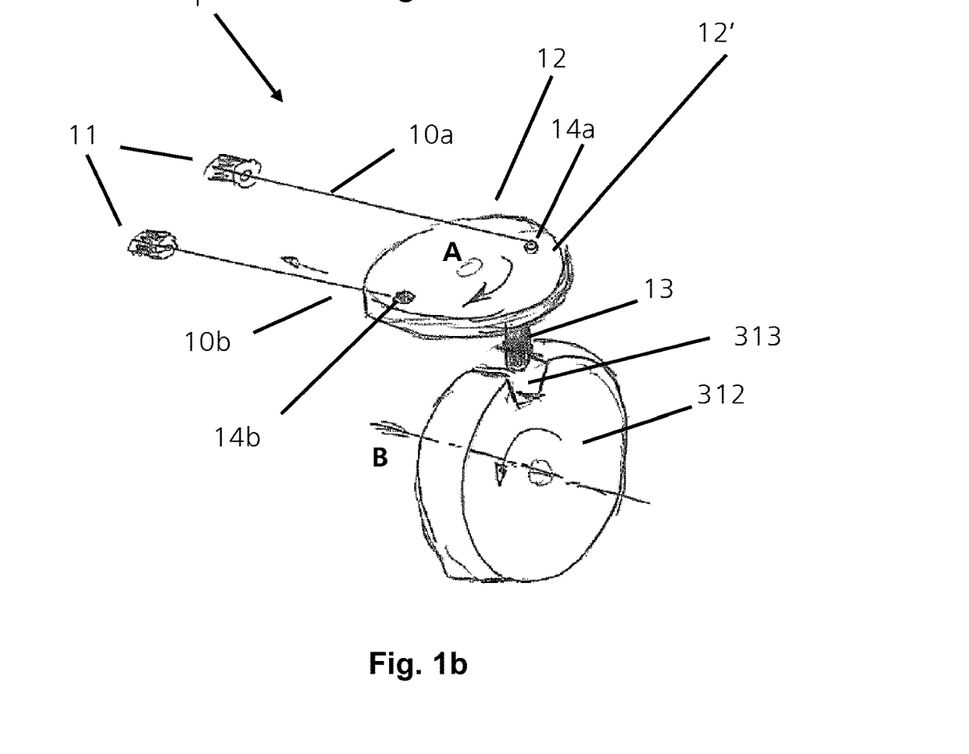

In the following, reference is first made to FIG. 1a and FIG. 1b, showing an exemplary embodiment of a valve drive unit 1 in a schematic top view (FIG. 1a) and perspective view (FIG. 1b), respectively.

The valve drive unit 1 (also referred to as "valve drive") includes a first SMA wire 10a and a second SMA wire 10b both of which are exemplarily arranged along a straight line and parallel to each other and form, in combination, a valve actuator. One end of each of the first and second SMA wire 10a, 10b is coupled to a pivoting member 12 via a corresponding SMA coupling structure 14a and 14b. Exemplarily, the SMA coupling structures (also referred to as "couplers") 14a, 14b are realized as pins that project from a (exemplarily disk-shaped) main body 12' of the pivoting member 12. The pivoting member 12 is pivotable around a fixed pivoting member axis A, and the SMA coupling structures 14a, 14b are arranged at opposite sides of the pivoting member axis A, with the distance to the pivoting member axis A each defining a lever arm. A (pulling) force that is exerted onto the first and then second SMA coupling structures 14a, 14b accordingly causes the pivoting member 12 to pivot around the pivoting member axis A in opposite directions, thereby transforming the linear movement of the SMA wires 10a, 10b into a pivoting movement of pivoting member 12. The opposite end of each of the first SMA wire 10a and the second SMA wire 10b is coupled to a fixed support structure 11. An exemplarily pin-shaped valve driver 13 is arranged at a distance from the pivoting member axis A and projects parallel to the pivoting member axis A from the main body 12'. The main body 12' and the valve driver 13 form, in combination, a crown wheel with the valve driver 13 as single tooth. The valve driver 13 and the SMA coupling structures 14a, 14b are formed integral with or are rigidly attached to the main body 12', thus forming common structural unit.

Together with the valve drive unit 1, a valve driver coupler 312 of a valve unit is shown. The valve driver coupler 312 exemplarily is realized by a disk that is pivotably arranged around a shutoff body axis B. The shutoff body axis B may coincide with a dosing unit axis (not shown). The valve driver coupler 312 includes a valve driver engagement structure 313. The valve driver engagement structure is realized as a slot in the circumference of the valve driver coupler 312 and is designed to releasably engage with the valve driver 13 with little play. The shutoff body axis B is exemplarily perpendicular to and intersects with the pivoting member axis A.

In the shown configuration, the second SMA wire 10b is exemplarily activated (heated) and thereby shortened. Consequently, the pivoting member 12 pivots around pivoting member axis A in the indicated direction. Because of the engagement between the valve driver 13 and the valve driver engagement structure 313, also the valve driver coupler 312 rotates around the shutoff body axis B as indicated. At the same time, the (not activated) first SMA wire 10a is passively lengthened. An alternative activation of the first SMA wire 10a with the second SMA wire 10b being un-activated would result in the pivoting member 12 and the valve driver coupler 312 move in the opposite direction, with the second SMA wire 10b being passively lengthened.

Figure 2:
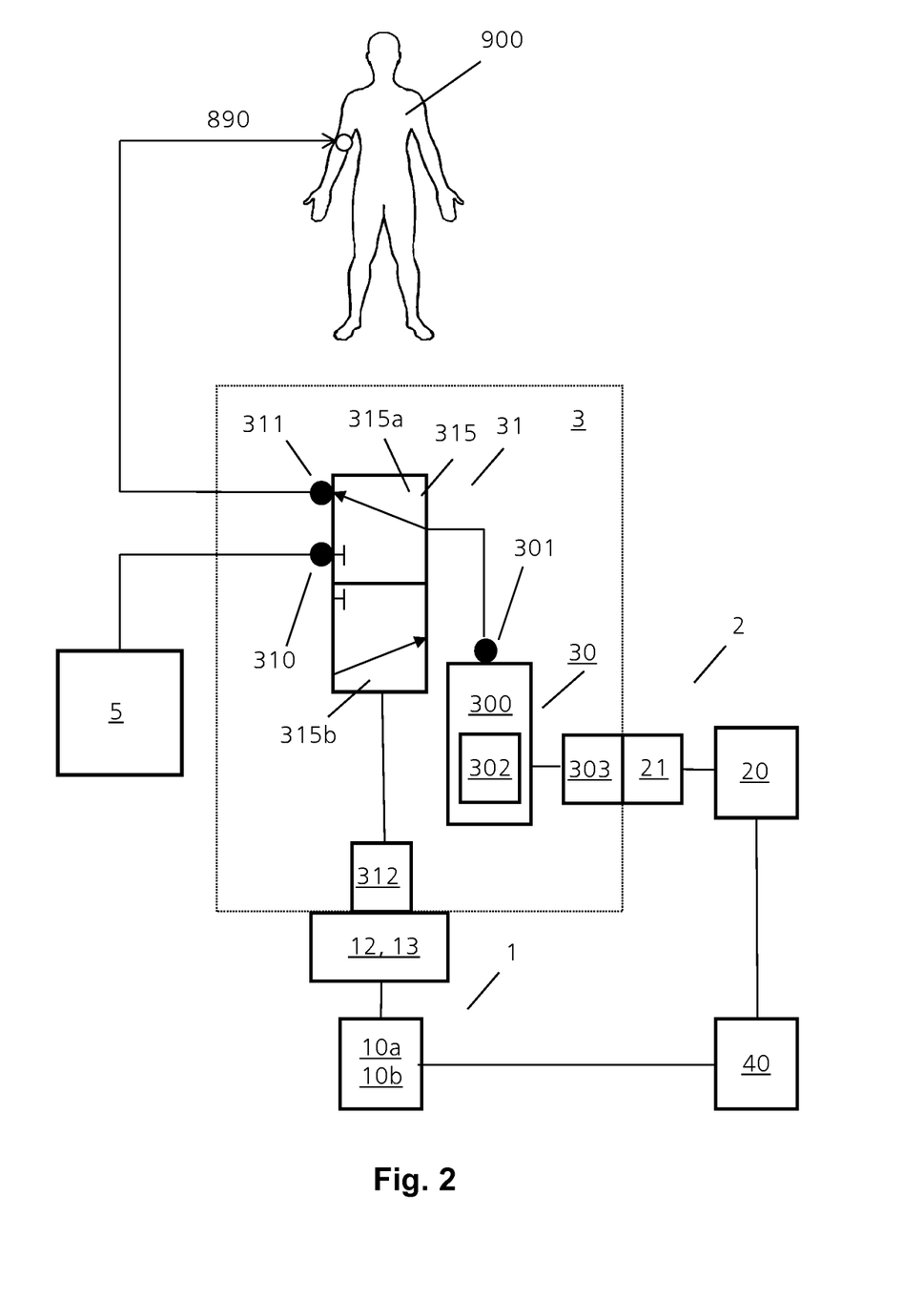
FIG. 2 shows an ambulatory infusion pump in a functional view.

In the following, reference is additionally made to FIG. 2. FIG. 2 shows an ambulatory infusion pump device in operative coupling to the patient in a symmetric functional view.

The ambulatory infusion pump device includes a dosing unit 3, and a drive unit, with the drive unit including a pump drive unit 2 and a valve drive unit 1. The ambulatory infusion pump device includes, in an operational state, a liquid drug reservoir 5. It is to be noted that only those structural and functional units are shown that are of particular relevance in view of the present disclosure. Other units, such as power supply, user interface etc. are typically present as well.

The dosing unit 3 includes a metering pump unit 30 and a valve unit 31. The metering pump unit 30 includes a dosing cylinder 300 and a piston 302 sealingly and slidingly arranged inside of the dosing cylinder 300 in a syringe-like way. In a proximal front wall of the dosing cylinder 300, a bore is arranged as pump port 301 that fluidly couples the inner volume of the dosing cylinder 300 with the valve unit 31. The valve unit 31 may alternatively be in a filling state, 315b (the shutoff body 315 in the filling position) or in a draining state 315a (the shutoff body 315 in the draining position). During operation, the valve unit 31 is repeatedly switched between those states. The reservoir 5 is fluidly coupled to the valve unit 31 via a filling port 310. The patient 900 is fluidly coupled to the valve unit 31 via a draining port 311 and an infusion site interface 890. It is noted that the infusion site interface 890 is exemplarily shown as integral with an infusion line, e.g., a catheter. Alternatively, the infusion pump device may be as a patch pump that is directly attached to a patient's body e.g., via an adhesive pad. Here, the infusion site interface may be a cannula.

The valve unit 31 includes a shutoff body 315 that is sealingly and rotatably arranged in a valve bearing. The shutoff body 315 includes a flow channel arrangement that realizes, as a function of a rotational position of the shutoff body, either the filling state 315b or the draining state 315a, respectively. The valve unit 31 is typically arranged in line with and proximal from the dosing unit 30. In a typical arrangement that is also assumed in the following, the shutoff body axis is parallel to and optionally coincides with a longitudinal axis of the dosing cylinder 300 along which the piston 302 is displaced. This arrangement, however, is not essential.

The dosing unit 3 further includes, as part of the valve unit 31, a valve driver coupler 312 for switching the valve unit 31 between the filling position, 315b, and the draining position 315a. Similarly, the dosing unit 3 includes, as part of the metering pump unit 30, a pump driver coupler 303 for displacing the piston 302 inside the dosing cylinder 300 as explained before. The pump driver coupler 303 may be fully or partly integral with the piston 302.

The operation of the metering pump unit 30 and the valve unit 31 are independent from each other. That is, the piston 302 may be displaced inside the dosing cylinder 300 without affecting the state of the valve unit 31. Likewise, the state of the valve unit 31 may be changed and switched without affecting the position of the piston 302 inside the dosing cylinder 300. Further, a valve switching between the filling state and the draining state does not involve a liquid displacement between the filling port 310 and the draining port 311 resulting from the movement of the shutoff body 315. Consequently, a valve switching does not involve the dosing of liquid to the patient. This aspect is of particular relevance because the controlled and metered dosing is carried out exclusively by controlled displacement of the piston 302. For highly concentrated drugs such as typical liquid insulin formulations, an unintended drug administration resulting from the valve switching may result in undesired and potentially severe medical complications.

In a typical arrangement, the dosing unit 3 with the metering pump unit 30 and the valve unit 31 is formed as a compact device and in an integral way. Therefore, the pump port 301 is, in contrast to the filling port 310 and the draining port 311, not accessible from outside the dosing unit 3.

With respect to the valve unit 31, it is further noted that FIG. 2 only shows the states 315a, 315b where either of the filling port 310 or the draining port 311 is coupled to the pump port 301. In a further intermediate state, however, all three ports 301, 310, 311 are closed, resulting in fluidic isolation.

The pump drive unit 2 includes the pump driver 21 that is designed to releasably engage the pump driver coupler 303 for displacing the piston inside the dosing cylinder 300 as explained before. The pump drive unit 2 further includes a pump actuator 20, typically a motor as mentioned before. The pump actuator may further include a reduction gear and/or a rotatory-to-linear transformation gear. The pump drive unit 2 is, as a whole, typically realized as spindle drive or screw drive that transforms a rotatory actuator movement into a reversible linear displacement movement of the pump driver 21, and, via the pump driver coupler, 303, of the piston 302. The pump driver 21 may be realized as plunger. The pump driver coupler 303 may be firmly attached to or integrated into a distal portion of the piston 302. The pump driver 21 and the pump driver coupler 303 are designed for push-pull-coupling, e.g., as bayonet coupling, snap-fit coupling, or the like. A reciprocal movement of the pump driver 21 results in a corresponding reciprocal piston movement in proximal or distal direction, respectively.

The valve drive unit 1 is designed in accordance with the present disclosure and includes a pivoting member 12 and a valve driver 13, and a first and second SMA wire, 10a, 10b, which form, in combination a valve actuator.

The pump actuator 20 and the first and second SMA wire 10a, 10b as valve actuator are coupled to control unit or control circuitry 40 which controls their operation.

The pump drive unit (also referred to herein as "pump drive") 2, the valve drive unit 1 and the control circuitry 40 typically belong to a common compact device that is also referred to as a "pump device" and forms the part of the ambulatory infusion pump device that is designed for an extended lifetime of a number of months, e.g., six months, or years, while the dosing unit 3 and the reservoir 5 are disposable and of substantially shorter lifetime.

Figure 3:
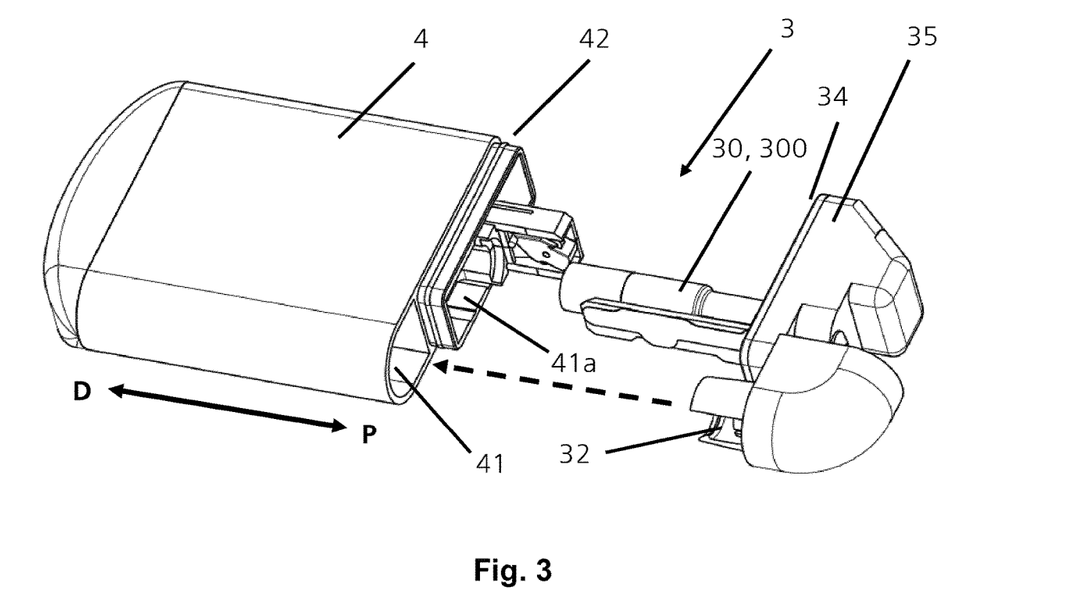
FIG. 3 shows an embodiment of a pump device and dosing unit in a perspective view.

In the following, reference is additionally made to FIG. 3 and FIG. 4. FIG. 3 shows major components of an exemplary embodiment of an ambulatory infusion pump in a schematic perspective view. The ambulatory infusion pump device is designed in accordance with FIG. 2 as discussed before.

In the figures, a proximal direction is indicated by "P" and a distal direction is indicated by "D." The ambulatory infusion pump comprises reusable pump device 4 that is designed for an extended lifetime of typically a number of years and therefore also referred to as "durable unit." By way of example, the ambulatory infusion pump is an insulin pump that is carried by a person with diabetes substantially continuously night and day. The overall size of the infusion pump is such that it can be carried concealed from view, for example, in a trousers pocket with the belt clip or the like, or can be attached to the body as a patch pump.

The pump device 4 has a housing (not referenced) which carries components such as a power supply, and a user interface. The pump device 4 in particular integrates the valve drive unit 1, the pump drive unit 2, and the control circuitry or control unit 40 as discussed before with reference to FIG. 2. The ambulatory infusion pump further comprises a dosing unit 3 that is designed for a lifetime of typically a number of days up to, e.g., two weeks. Resulting from their different application time, the pump device 4 and in particular the pump drive unit 2 on the one hand and the dosing unit 3 on the other hand are designed for releasable mechanical and operational coupling.

Figure 4:
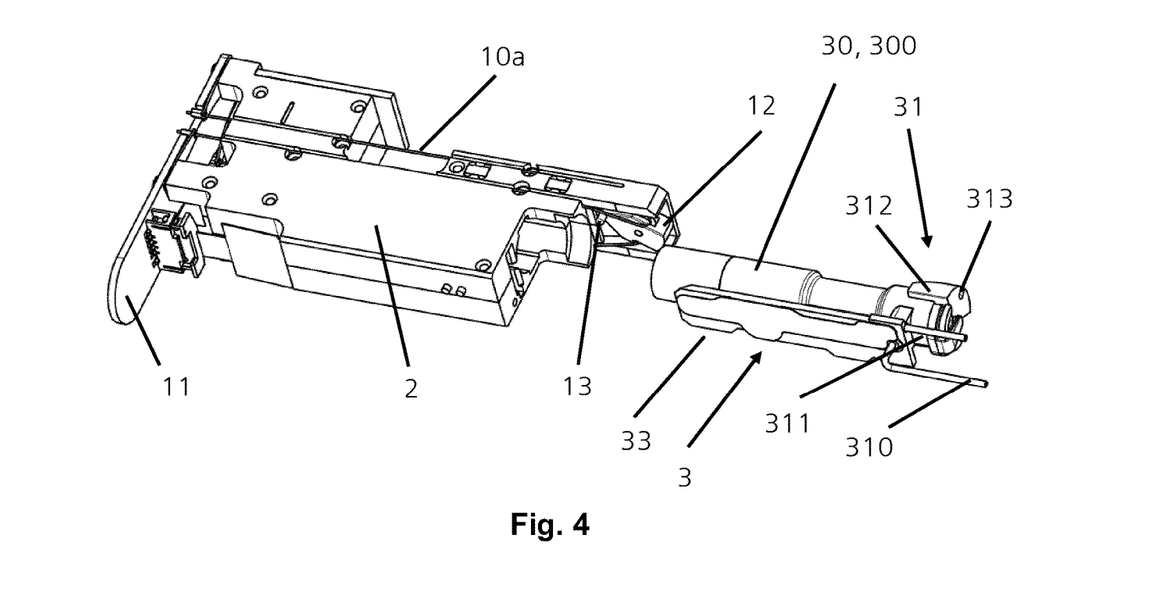
FIG. 4 shows the device of FIG. 3 with the housing removed in a perspective view.

Both FIG. 3 and FIG. 4 show the ambulatory infusion pump with a pump device 4 and a dosing unit 3 being somewhat spaced apart from each other, i.e., in an unconnected state, but in a relative orientation that corresponds to the orientation during application. In contrast to FIG. 4, housing components of the pump device 4 and the disposable unit 3 are removed.

In addition to the components that are shown in FIGS. 2, 3, the ambulatory infusion pump includes, in an operational state, the drug reservoir 5. The shown embodiment is designed for use in combination with a cylindrical drug cartridge of, e.g., 1.5 ml to 3 ml filling volume. The drug cartridge couples with the dosing unit 3 via a cartridge coupler 32 that includes a mechanical and fluid interface structure In a coupled state, the cartridge extends along the proximal-distal direction. The fluid interface structure includes a hollow cannula (not visible) to pierce a septum of the drug cartridge, thus fluidly coupling the inner volume of the drug cartridge with the inlet port 310 of the dosing unit 3.

Coupling of the pump device 4 and the dosing unit 3 is achieved via a linear movement of the dosing unit 3 relative to the pump device 4 in a distal direction, as indicated by a dashed arrow. The pump device 4 includes a cartridge receptacle 41 that receives the drug cartridge, and a dosing cylinder receptacle 41a that receives the metering pump unit 30 of the dosing unit 3 for the application time of the dosing unit 3 and the cartridge.

For the mechanical coupling or mounting, the pump device 4 and the dosing unit 3 are provided with a pump device mounting structure 42 that is designed to receive the pump cylinder 300 and an optional sensor assembly 33. In an assembled state, the pump device 4 and the dosing unit 3 form, in combination, a watertight or water protected assembly during application. Decoupling is carried out by a corresponding linear counter-movement of the dosing unit 3 relative to the pump device 4 in the proximal direction, potentially involving the unlocking or releasing of snap fit elements, catches. The optional sensor assembly 33 comprises an elongated plate that extends parallel to the dosing cylinder 300 and may include, e.g., a fluid pressure transfer membrane, a flow sensor or flow detector, and/or an air sensor. As mating counter-element to the pump device mounting structure 42, the dosing unit 3 includes a corresponding dosing unit mounting structure. In this embodiment, a proximal end of the sensor assembly 33 is connected to other components of the dosing unit 3, in particular the metering pump unit 30 and a disposable housing 35. The disposable housing 35 includes, at its distal end, a circumferential seal 34.

In addition to the aforementioned elements, the dosing unit 3 includes the metering pump unit 30 and the valve unit 31. The whole dosing unit 3 is favorably designed and provided as a common integral unit. The dosing unit 3 is realized as inline arrangement with the valve unit 31 being arranged proximal from the metering pump unit 30. The drug reservoir, in particular drug cartridge may be provided already coupled to the cartridge coupler 32, or may be separate and coupled by the user. The overall arrangement and design of the dosing unit 30 is realized in accordance with FIG. 2 and the corresponding description.

Figure 5:
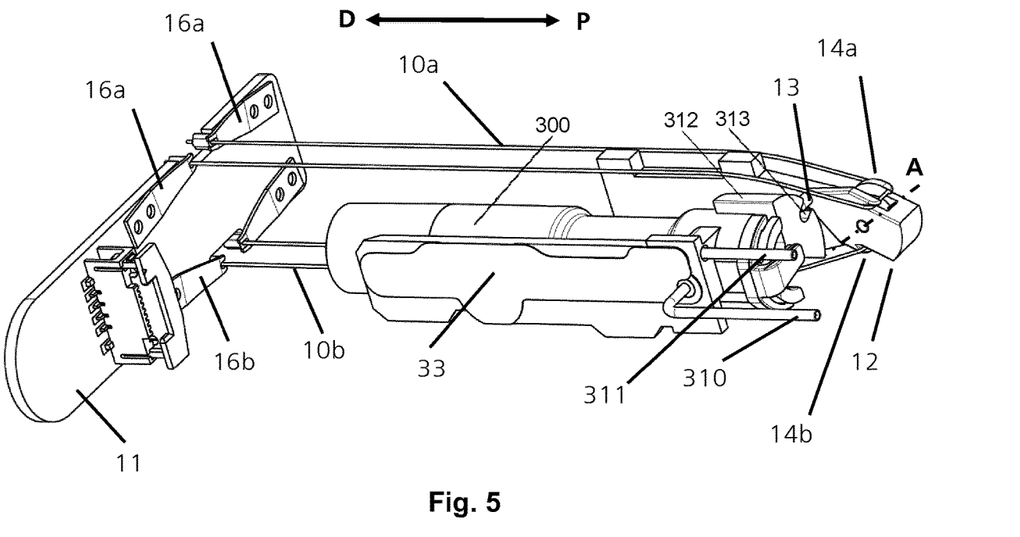
FIG. 5 shows a further embodiment of a valve drive unit in operative coupling with a dosing unit in a perspective view.

In the following, reference is additionally made to FIG. 5, illustrating the cooperation between the valve drive unit 1 and the valve unit 31. The valve driver coupler 312 includes the slot-shaped valve driver engagement structure 313 that is discussed further below in more detail and engages, in the coupled state as shown in FIG. 5, the pin-shaped valve driver 13 that projects from the body of the pivoting member 12 and into the valve driver engagement structure 313. The shutoff body 315 of the valve unit 31 is formed integrally with the valve driver coupler 312 and is itself not visible in FIGS. 3, 4.

In this shown example, the dosing unit 3 is realized as an inline design, with the piston displacement axis (corresponding to the longitudinal axis of the dosing cylinder 300 and extending between distal and proximal) being coincident with the shutoff body axis B (see also FIGS. 1, 7), as explained before in the context of FIG. 2.

In contrast to the embodiment of FIGS. 1a, 1b, the first SMA wire 10a and the second SMA wire 10b each are substantially U-shaped. For each of the first SMA wire 10a and the second SMA wire 10b, the base of the U-shaped SMA wires (the area where both legs of the "U" meet) is coupled to the pivoting member 12 via SMA coupling member 14a, 14b in the form of hooks in which the bases of the first SMA wire 10a and the second SMA wire rest. The hooks are, like the pins of the embodiment of FIG. 1a, 1b, arranged on opposite sides of the pivoting member axis A, thus transforming a shortening of the first SMA wire 10a and alternately the second SMA wire 10b into pivoting movements in opposite directions, with the other of the first SMA wire 10a and second SMA wire 10b being passively length-ened. Via the engagement between the valve driver 13 and the valve driver coupler 312, via the engagement structure 313, the pivoting movement of the pivoting member 12 results in a corresponding pivoting of the valve driver coupler 312 and the shutoff body 315 around the shutoff body axis B.

From the pivoting member 12, the legs of the SMA wires 10a, 10b extend parallel in distal direction and are separately coupled to the support structure 11 which is exemplarily realized as printed circuit board. The support structure 11 may be part of or rigidly connected to other parts of the pump structure and is in particular rigidly coupled to the housing of the pump device 4. The support structure is sufficiently stiff to absorb the forces that are exerted by the first and second SMA wire 10a, 10b without significant deformation.

The pivoting member 12 as a whole or at least the SMA coupling structures 14a, 14b are favorably made from metal or metallized such that the heating current through the SMA wires 10a, 10b is shortcut as explained before in the general description.

Figure 6:
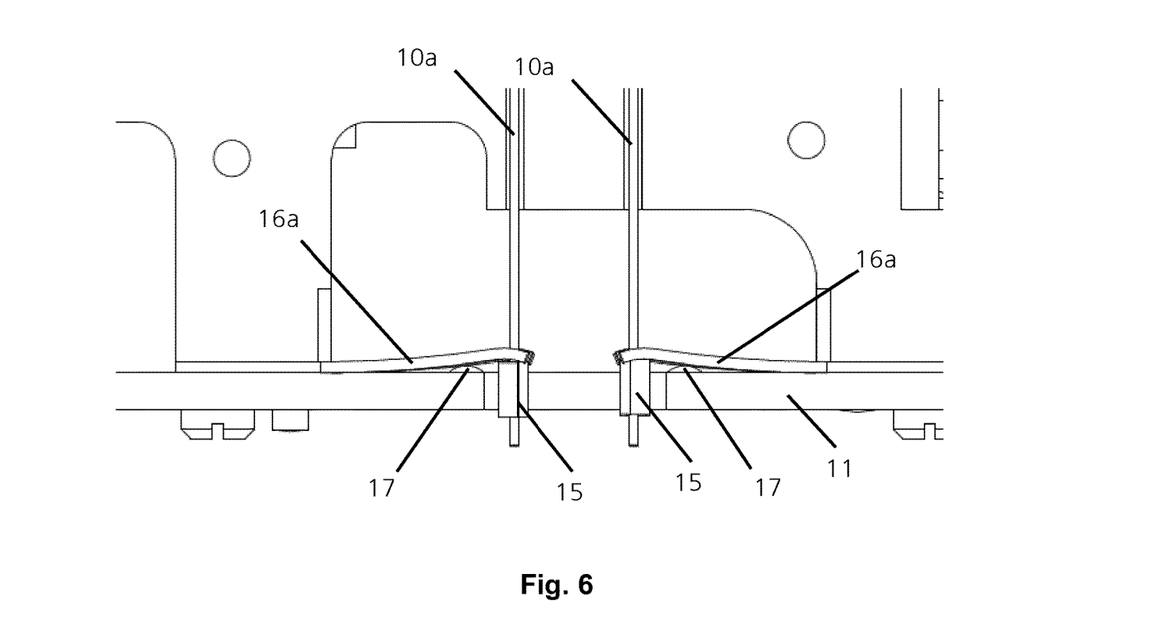
FIG. 6 shows a section of a valve drive unit.

In the following, reference is additionally made to FIG. 6. FIG. 6 shows the distal end section of the first SMA wire 10a and the support structure 11 in a detailed view. Close to its free ends, the legs of the SMA wire 10a, 10b each have a thickening which is exemplarily realized as a sleeve 15 that is firmly connected to the corresponding SMA wire, e.g., by crimping or soldering. Via the sleeve 15, each leg of the first SMA wire 10a, is hooked in an exemplarily slot-shaped recess (not referenced) that is arranged at a free end section of a first leaf spring 16a. The opposite end of the first leaf springs 16a is firmly attached to the support structure 11, e.g., via screwing, riveting, clamping, or the like. Close to the free end, each of the two leaf springs rests on a support member that is exemplarily realized as dome-shaped rivet 17. As best visible in FIG. 4, the same principle is applied to the second SMA wire 10b that is coupled to the support structure via second leaf springs 16b.

In a non-elongated state of the SMA wire 10a, the first leaf springs 16a rest on the corresponding rivets 17 with a nominal contact force that acts in distal direction and is at the same time a threshold force and switching force as explained before in the general description. In combination, the first leaf springs 16a accordingly serve as first spring structure that strains the first SMA wire 10a by exerting a force in distal direction. Similarly, the second leaf springs 16b serve as second spring structure that strains the second SMA wire 10b.

The first and second leaf springs 16a, 16b and the rivets 17 are typically made from metal and therefore are conductive and/or have a conductive coating. The valve drive control circuitry (a functional component of the control unit or control circuitry 40, see FIG. 2) is connected to the rivets 17. For activating the first SMA wire 10a, an electric power supply is connected to the rivets 17, thereby establishing a current flow from the power supply, via one of the rivets 17 and the associated first leaf spring 16a, the first SMA wire 10a, the other first leaf spring 16a and associated rivet 17, and back to the power supply.

As explained before, the shortening of the activated first SMA 10a wire results in a pivoting movement of the pivoting member 12 unit further movement is blocked. At the same time, the contact force between the first leaf springs 16a and the associated rivets 17 is reduced due to the pulling force that is exerted by the first SMA wire 10a. Further reducing the length of the activated first SMA wire 10a results in the first leaf springs 16a being lifted off and loosing contact with the associated rivets 17, resulting in the current flow being interrupted and heating of the first SMA wire 10a stops. The same applies for the second SMA wire 10b in an analogous way. The leaf springs 16a, 16b accordingly serve as end position switches or end position sensors that detect if the shutoff body 315 assumes either of its end positions.

A further advantageous effect of the shown arrangement occurs when the whole pump device 4 (or a drive unit as pre-assembled sub-unit) is exposed to a high temperature, e.g., during storage or transport, beyond the activation temperature. As explained before, both the first SMA wire 10a and the second SMA wire 10b will be activated and will accordingly shorten. As apparent, e.g., from FIG. 4, such situation results in a considerable mechanical stress on all of the support structure 11, the SMA wires 10a, and the pivoting member 12, including its bearing. Without the elasticity of the leaf springs 16a, 16b, the structure may well be damaged in this situation. Both the first and second leaf springs 16a, 16b, however, will be elongated in this case and be lifted off the rivets 17, thereby limiting the pulling force that is exerted by the first and second SMA wires 10a, 10b to an acceptable value within the design limits.

Figure 7:
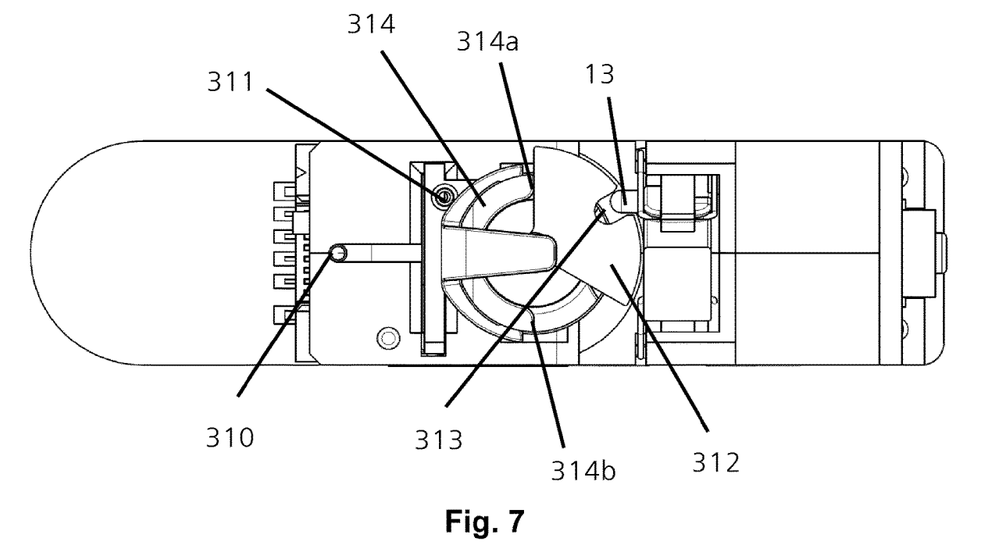
FIG. 7 shows a front view of a pump device and a dosing unit.

In the following, reference is additionally made to FIG. 7. FIG. 7 shows the arrangement of FIG. 4 in a front view (with the viewing direction being from proximal to distal), with the valve driver 13 engaging the engagement structure 313 of the valve driver coupler 312.

The dosing unit 3 includes a blocking structure that is exemplarily realized as ring section 314 concentric with the dosing cylinder 300 and the shutoff body axis B (exemplarily identical with the dosing cylinder axis and the piston displacement axis). The ends 314a, 314b of the ring section 314 serve as valve blocks that block further movement of the valve driver coupler 312—and, in an engaged state, of the pivoting member 12 with valve driver 13—upon a corresponding surface of the valve driver coupler 312 hitting the block. In FIG. 7, the valve driver coupler 312 is shown in a configuration where it hits the upper valve block 314a.

Figure 8:
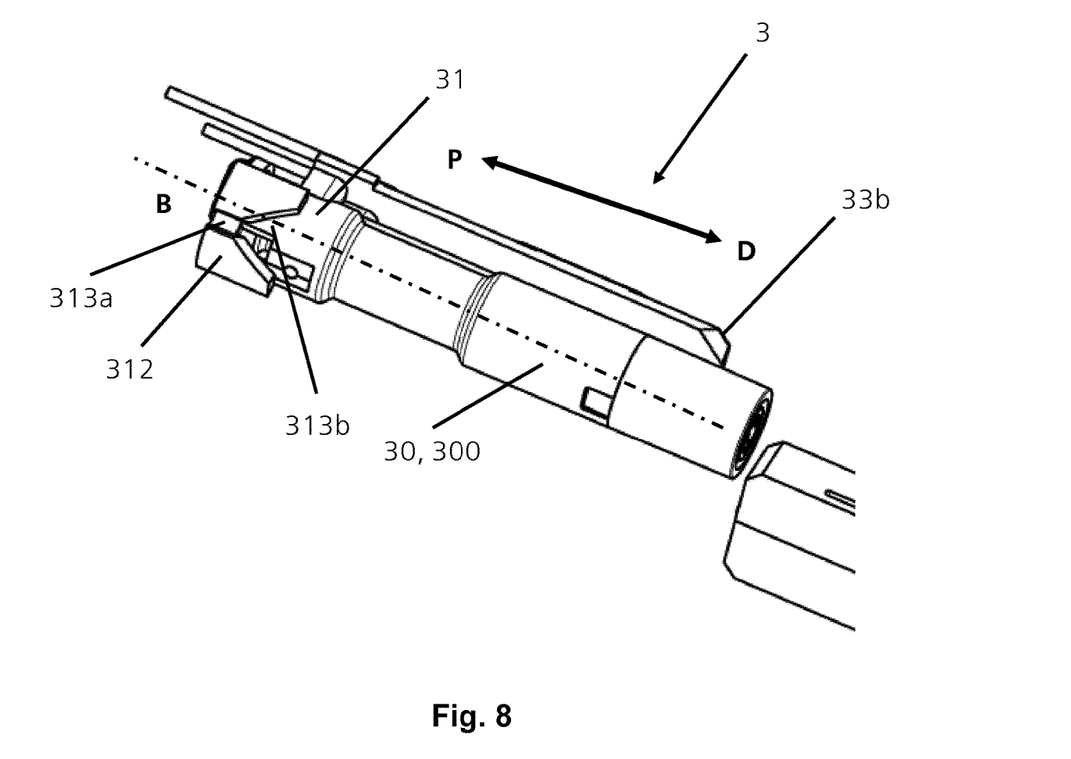
FIG. 8 shows a dosing unit in a perspective view.

In the following, reference is additionally made to FIG. 8. FIG. 8 shows the dosing unit 3 in a perspective view. It can be seen that the engagement structure 313 is a funnel-shaped recess, having a proximal portion 313a with parallel sidewalls and a trapezoidal distal portion 313b with converging sidewalls. At the distal end, the width of the distal portion 313b is widest. At the proximal end of the distal portion 313b, its width corresponds to the width of the proximal portion 313 a. When coupling the dosing unit 3 with the pump device 4 includes the dosing cylinder receptacle 41a (see FIG. 3), the valve driver coupler 13 (not visible in FIG. 8) will first enter the trapezoidal distal portion 313b and be guided into the proximal portion 313a where it stays for subsequent operation. During this insertion and coupling process, the pivoting member 12 with the valve driver 13 and the valve driver coupler 312 are aligned with respect to each other as explained before.

When the coupling is finished (and the dosing cylinder 300 is situated in the dosing cylinder receptacle 41a), the valve driver 12 and the valve driver coupler 312 are in correct engagement and relative alignment, but in a generally undefined state. That is, the shutoff body (and accordingly the valve driver 12 and the valve driver coupler 312) may be in any position between the filling position and the draining position. When activating the valve drive 1 for the first time, less than a full stroke will accordingly be required until the shutoff body assumes the filling position or the draining position as either of its end positions, and further movement is blocked. In the here-described embodiment, reaching of either of the end positions automatically results in an interruption of the power supply. Alternatively or additionally, however, a monitoring sensor that monitors the position of the shutoff body 315 (or, equivalently, of the valve driver coupler 312), such as dedicated end switches, light barrier, or the like may be present as part of the control unit or control circuitry 40.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A valve drive, comprising:
    a pivoting member pivotably arranged around a pivoting member axis, the pivoting member including a valve driver spaced from the pivoting member axis;
    first and second SMA wires coupled to the pivoting member and configured to be alternatively activated, wherein activation of the first SMA wire causes the pivoting member to pivot in a first direction and activation of the second SMA wire causes the pivoting member to pivot in a second direction opposite the first direction;
    a valve driver coupler releasably engageable with the valve driver, wherein, in an engaged state, pivoting of the pivoting member is transmitted to the valve driver coupler via the valve driver; and
    wherein the first SMA wire is elastically secured to a support via a first spring structure at a location on the first SMA wire that is at a distance from where the first SMA wire is coupled to the pivoting member and the second SMA wire is elastically secured to the support via a second spring structure at a location on the second SMA wire that is at a distance from where the second SMA wire is coupled to the pivoting member.

2. The valve drive according to claim 1, wherein an activation of the first SMA wire lengthens the second SMA wire and an activation of the second SMA wire lengthens the first SMA wire.

3. The valve drive according to claim 1, wherein the first and second SMA wires are each U-shaped.

4. The valve drive according to claim 1, wherein the first spring structure comprises a first leaf spring and the second spring structure comprises a second leaf spring.

5. The valve drive according to claim 1, wherein the first spring structure and the second spring structure limit forces that may be exerted by the first and second SMA wires, respectively.

6. The valve drive according to claim 1, wherein the pivoting member includes a first SMA coupling structure coupled to the first SMA wire and a second SMA coupling structure coupled to the second SMA wire, wherein the first and second SMA coupling structures are arranged on opposite sides of the pivoting member axis (A).

7. The valve drive according to claim 1, wherein the valve driver is a meshing pin.

8. A drive assembly for use with a dosing unit, the drive assembly comprising:
    a pump drive having a pump actuator and a pump driver coupled to the pump actuator, wherein the pump driver is configured to releasably engage a piston of the dosing unit for transmitting a pump driving force and/or pump driving torque from the pump actuator to the piston to thereby displace the piston in a dosing cylinder of the dosing unit; and
a valve drive according to claim 1.

9. An assembly comprising:
a drive assembly having the valve drive according to claim 1 and a pump drive;
a dosing unit configured to releasably couple to the drive assembly, the dosing unit comprising:
  a metering pump unit having a dosing cylinder with a piston slidingly and sealingly arranged therein, the piston configured to engage with a pump driver of the pump drive;
  a valve unit having a filling port configured for fluid coupling with a liquid drug reservoir, a draining port configured for fluid coupling with an infusion site interface, and a shutoff body that is pivotable between (i) a filling position in which the shutoff body fluidly couples the filling port to the dosing cylinder and (ii) a draining position in which the shutoff body fluidly couples the dosing cylinder with the draining port; and
wherein the valve driver coupler is coupled to or integral with the shutoff body.

10. The assembly according to claim 9, wherein the valve driver coupler includes a funnel-shaped engagement structure that aligns the valve driver coupler with the valve driver during a relative engagement movement between the drive assembly and the dosing unit.

11. The assembly according to claim 9, wherein the valve unit includes valve blocks configured to block pivoting of the shutoff body beyond the filling position and the draining position.

12. A valve drive, comprising:
a pivoting member pivotably arranged around a pivoting member axis, the pivoting member including a valve driver spaced from the pivoting member axis;
first and second SMA wires coupled to the pivoting member and configured to be alternatively activated, wherein activation of the first SMA wire causes the pivoting member to pivot in a first direction and activation of the second SMA wire causes the pivoting member to pivot in a second direction opposite the first direction;
a valve driver coupler releasably engageable with the valve driver, wherein, in an engaged state, pivoting of the pivoting member is transmitted to the valve driver coupler via the valve driver; and
wherein the first SMA wire is connected at a first coupling to a first spring structure, the first spring structure being disposed between the first SMA wire and the support and wherein the first spring structure is configured to maintain the first coupling between the first SMA wire and the first spring structure in a constant position when a first force that is exerted by the first SMA wire is below a first threshold force and wherein, when the first force exceeds the first threshold force, the first spring structure is deflected and the first coupling moves to thereby limit the first force exerted by the first SMA wire; and
wherein the second SMA wire is connected at a second coupling to a second spring structure, the second spring structure being disposed between the second SMA wire and the support and wherein the second spring structure is configured to maintain the second coupling between the second SMA wire and the second spring structure in a constant position when a second force that is exerted by the second SMA wire is below a second threshold force and wherein, when the second force exceeds the second threshold force, the second spring structure is deflected and the second coupling moves to thereby limit the second force exerted by the second SMA wire.

13. The valve drive according to claim 12 wherein the first SMA wire is coupled to the pivoting member at a distance from the first coupling and wherein the second SMA wire is coupled to the pivoting member at a distance from the second coupling.

14. A valve drive, comprising:
a pivoting member pivotably arranged around a pivoting member axis, the pivoting member including a valve driver spaced from the pivoting member axis;
first and second SMA wires coupled to the pivoting member and configured to be alternatively activated, wherein activation of the first SMA wire causes the pivoting member to pivot in a first direction and activation of the second SMA wire causes the pivoting member to pivot in a second direction opposite the first direction;
a valve driver coupler releasably engageable with the valve driver, wherein, in an engaged state, pivoting of the pivoting member is transmitted to the valve driver coupler via the valve driver;
wherein the first SMA wire is coupled to a support via a first spring and the second SMA wire is coupled to the support via a second spring;
wherein the first spring comprises a first switch configured to interrupt a current supply of the first SMA wire upon a first force that is exerted by the first SMA wire on the support exceeding a first switching force; and
the second spring comprises a second switch configured to interrupt a current supply of the second SMA wire upon a second force that is exerted by the second SMA wire on the support exceeding a second switching force.

15. A drive assembly for use with a dosing unit, the drive assembly comprising:
a pump drive having a pump actuator and a pump driver coupled to the pump actuator, wherein the pump driver is configured to releasably engage a piston of the dosing unit for transmitting a pump driving force and/or pump driving torque from the pump actuator to the piston to thereby displace the piston in a dosing cylinder of the dosing unit; and
a valve drive comprising:
  a pivoting member pivotably arranged around a pivoting member axis, the pivoting member including a valve driver spaced from the pivoting member axis;
  first and second SMA wires coupled to the pivoting member and configured to be alternatively activated, wherein activation of the first SMA wire causes the pivoting member to pivot in a first direction and activation of the second SMA wire causes the pivoting member to pivot in a second direction opposite the first direction;
  a valve driver coupler releasably engageable with the valve driver, wherein, in an engaged state, pivoting of the pivoting member is transmitted to the valve driver coupler via the valve driver; and
wherein the pump driver engages the piston and the valve driver engages the valve driver coupler via a common relative engagement movement.

* * * * *